(12) United States Patent
Yamamoto et al.

(10) Patent No.: US 6,787,665 B2
(45) Date of Patent: Sep. 7, 2004

(54) PRODUCTION METHOD OF SUBSTITUTED BENZENES

(75) Inventors: Noboru Yamamoto, Kawanishi (JP); Sanshiro Matsuo, Osaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 66 days.

(21) Appl. No.: 10/337,533

(22) Filed: Jan. 7, 2003

(65) Prior Publication Data

US 2003/0130538 A1 Jul. 10, 2003

(30) Foreign Application Priority Data

Jan. 10, 2002 (JP) ........................ 2002-003180

(51) Int. Cl.$^7$ ......................... C07C 67/02; C07C 41/00; C07C 43/02; C07C 43/20
(52) U.S. Cl. ...................... 560/254; 568/649
(58) Field of Search ........................ 560/254; 568/649

(56) References Cited

U.S. PATENT DOCUMENTS

| 5,872,137 A | 2/1999 | Sakamoto et al. |
| 5,922,880 A | 7/1999 | Sakamoto et al. |

FOREIGN PATENT DOCUMENTS

EP    0 272 674 A2    6/1988

*Primary Examiner*—Richard L. Raymond
*Assistant Examiner*—Zachary C. Tucker
(74) *Attorney, Agent, or Firm*—Akin Gump Strauss Hauer & Feld, LLP

(57) ABSTRACT

An ester compound of formula (1)

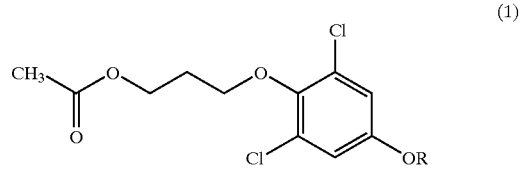

can be produced by making a compound given by formula (2):

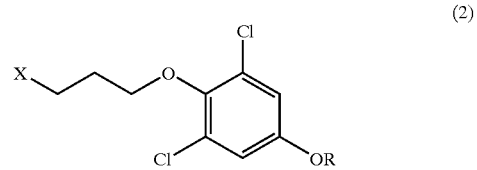

react with an alkali metal salt of acetic acid in the presence of an aromatic hydrocarbon, and the obtained ester compound of formula (1) react with an alkali metal hydroxide and water to give a 3-phenoxypropanol compound of formula (3):

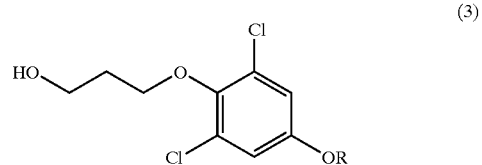

8 Claims, No Drawings

PRODUCTION METHOD OF SUBSTITUTED BENZENES

FIELD OF THE INVENTION

The present invention relates to production methods of 3,5-dichloro-4-(3-hydroxypropoxy)-1-substituted-benzenes and 3,5-dichloro-4-(3-acetyloxypropoxy)-1-substituted-benzenes.

BACKGROUND ARTS

In U.S. Pat. No. 5,827,137 and U.S. Pat. No. 5,922,880, 3,5-dichloro-4-(3-hydroxypropoxy)-1-substituted-benzenes are described as intermediates for producing a kind of dihalopropene compounds having insecticidal/acaricidal activity. Further, described is a production method of the 3,5-dichloro-4-(3-hydroxypropoxy)-1-substituted-benzenes by making a 3,5-dichloro-4-(3-bromopropoxy)-1-substituted-benzene compound react with benzoic acid and potassium carbonate in the presence of N,N-dimethylformamide to give a 3,5-dichloro-4-(3-benzoyloxypropoxy)-1-substituted-benzene compound and then allowing the product to be hydrolyzed in said publications.

However, the first step that is the reaction of the 3,5-dichloro-4-(3-bromopropoxy)-1-substituted-benzene compound with benzoic acid and potassium carbonate needs N,N-dimethylformamide, which is desired to avoid the use of a large amount in an industrial production, as a solvent. (cf. U.S. Pat. No. 5,922,880, col. 107) On the other hand, when said reaction is carried out in an aromatic hydrocarbon which is available in an industrial production, it needs a large amount of the solvent because the solubility of the obtained 3,5-dichloro-4-(3-benzoyloxypropoxy)-1-substituted-benzene compound in the aromatic hydrocarbon is low. Therefore, it is not beneficial in an industrial production.

The object of the present invention is to provide industrially advantageous methods for producing 3,5-dichloro-4-(3-hydroxypropoxy)-1-substituted-benzenes which are useful as intermediates for producing an insecticidal/acaricidal compounds and for producing 3,5-dichloro-4-(3-acetyloxypropoxy)-1-substituted-benzenes which are their precursors.

SUMMARY OF THE INVENTION

The advantageous method for producing 3,5-dichloro-4-(3-hydroxypropoxy)-1-substituted-benzenes in an industrial production was studied and found that 3,5-dichloro-4-(3-acetyloxypropoxy)-1-substituted-benzenes can be produced by making 3,5-dichloro-4-(3-halopropoxy)-1-substituted-benzenes react with an alkali metal salt of acetic acid in the presence of an aromatic hydrocarbon and that the 3,5-dichloro-4-(3-acetyloxypropoxy)-1-substituted-benzenes can be lead to 3,5-dichloro-4-(3-hydroxypropoxy)-1-substituted-benzenes. The method does not need N,N-dimethylformamide as a solvent or a large amount of solvent.

Namely, the present invention provides a production method of an ester compound given by formula (1):

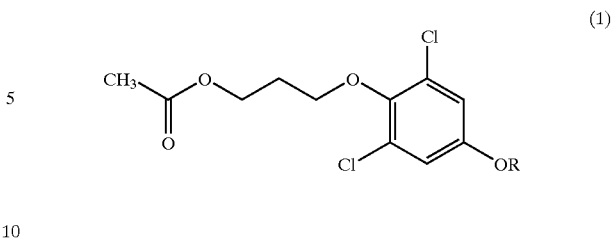

wherein R represents a 3,3-dihalo-2-propenyl group or a benzyl group optionally substituted by halogen atom(s), which comprises making a compound given by formula (2):

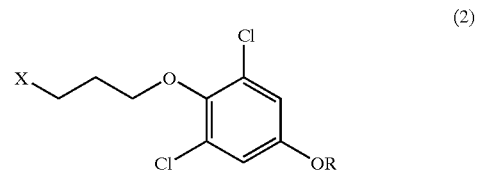

wherein X represents a chlorine atom or bromine atom and R means as described below react with an alkali metal salt of acetic acid in the presence of an aromatic hydrocarbon (hereinafter, referred to as the production method 1 of the present invention).

The present invention also provides a production method of a 3-phenoxypropanol compound given by formula (3):

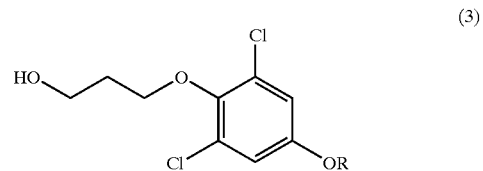

wherein R means as defined below, which comprises making a compound given by formula (2):

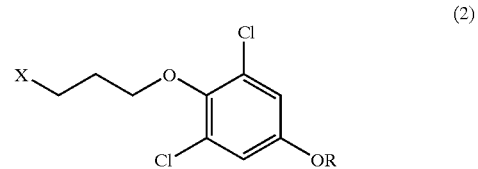

wherein X represents a chlorine atom or bromine atom and R represents a 3,3-dihalo-2-propenyl group or a benzyl group optionally substituted by halogen atom(s), react with an alkali metal salt of acetic acid in the presence of an aromatic hydrocarbon, and then making the product react with an alkali metal hydroxide and water (hereinafter, referred to as the production method 2 of the present invention, further the combination of the method 1 of the present invention together with the method 2 of the present invention is referred to as the production methods of the present invention).

Furthermore, the present invention provides an ester compound given by formula (1):

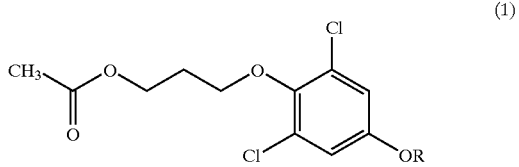

wherein R represents a 3,3-dihalo-2-propenyl group or a benzyl group optionally substituted by halogen atom(s).

The ester compounds given by formula (1) are hydrolyzed in alkali water to give the 3-phenoxypropanol compounds given by formula (3) those are useful as intermediates for producing the above-mentioned insecticidal/acaricidal compounds.

DETAILED DESCRIPTION OF THE INVENTION

In the present invention, examples of the 3,3-dihalo-2-propenyl group include 3,3-dichloro-2-propenyl group and 3,3-dibromo-2-propenyl group. The benzyl group optionally substituted by halogen atom(s) is exemplified by a benzyl groups whose hydrogen atom(s) on its benzene ring may be substituted by at least one halogen atom, and the typical examples are benzyl group and 4-chlorobenzyl group.

The production method 1 of the present invention is explained at first.

The production method 1 of the present invention is characterized by making the compound given by formula (2) react with an alkali metal salt of acetic acid in the presence of an aromatic hydrocarbon.

Examples of the aromatic hydrocarbon used for the reaction include toluene, xylene, mesitylene and ethylbenzene. The amount of the aromatic hydrocarbon used for the reaction is usually in the range of 0.1 to 10 parts by weight based on 1 part by weight of the compound given by formula (2), preferably 0.1 to 1 part by weight, more preferably 0.1 to 0.25 part by weight, and furthermore preferably 0.1 to 0.2 part by weight based on 1 part by weight of the compound given by formula (2) in the view of the reaction rate.

Examples of the alkali metal salt of acetic acid used for the reaction include sodium acetate and potassium acetate. The alkali metal salt of acetic acid can also be prepared by mixing acetic acid with an alkali metal hydroxide in the reaction mixture. The amount of the alkali metal salt of acetic acid used for the reaction is usually in the range of is usually in the ratio of 1 to 2 mols based on 1 mol of the compound given by formula (2), preferably 1.3 mols or more in the view of the reaction rate, and preferably 1.7 mols or less in the view of the economical reason.

It is preferable that the reaction is carried out in the presence of a phase transfer catalyst in the view of the yield. In such cases, examples of the phase transfer catalysts used for the reaction include tertiary ammonium salts such as tetra-n-butylammonium bromide, tetra-n-butylammonium chloride and so on. The amount of the phase transfer catalyst used for the reaction is usually in the ratio of 0.01 to 0.1 mol based on 1 mol of the compound given by formula (2).

The reaction temperature is usually in the range of 20 to 120° C. Among them, it is preferably 100° C. or more in the view of the reaction rate.

The reaction can be, for example, carried out by mixing the compound given by formula (2) with the aromatic hydrocarbon, adding the alkali metal salt of acetic acid and optionally the phase transfer catalyst thereto, and stirring. In that case, the alkali metal salt of acetic acid can be added at once or portionwise. The reaction can also be carried out by adding acetic acid and an alkali metal hydroxide to a mixture of the compound given by formula (2) and the aromatic hydrocarbon, and stirring.

The proceeding status of the reaction can be confirmed by means for analyzing the reaction product such as high performance liquid chromatography and the like.

After the reaction, the ester compound given by formula (1) can be isolated by work-up procedures, for example, obtaining an organic layer by water-organic solvent phase separation of the reaction mixture, and concentrating the organic layer.

Further, the reaction mixture can be provided for the next steps without performing the work-up procedures.

Next, the production method 2 of the present invention is explained below.

The production method 2 of the present invention is characterized by making the compound given by formula (2) react with an alkali metal salt of acetic acid in the presence of an aromatic hydrocarbon, followed by making the product react with an alkali metal hydroxide and water.

Namely, the method 2 of the present invention comprises the first step of making the compound given by formula (2) react with an alkali metal salt of acetic acid in the presence of an aromatic hydrocarbon solvent, and the second step of making the product in the first step react with an alkali metal hydroxide and water.

The reaction of the first step in the production method 2 of the present invention can be performed in the same condition as the production method 1 of the present invention. After the reaction of the first step, work-up procedures are performed to be isolated the ester compound given by formula (1). The isolated ester compound given by formula (1) can be provided for the second step. Further, the reaction mixture in the first step can also be provided to the second step without the work-up procedures.

The reaction of second step is usually performed in the presence of a solvent or in the absence of a solvent.

Examples of the solvent used for the reaction include aromatic hydrocarbons such as toluene, xylene, mesitylene, ethylbenzene and so on; alcohols such as methanol, ethanol, propanol and so on; and mixtures thereof.

Examples of the alkali metal hydroxide used for the reaction include sodium hydroxide and potassium hydroxide. The amount of the alkali metal hydroxide used for the reaction is usually 1 to 1.25 mols based on 1 mol of the ester compound given by formula (1), or is usually 1 to 1.25 mols based on 1 mol of the ester compound given by formula (2) in case that the second step is carried out without isolating the product after the first step.

The amount of water used for the reaction is usually 1 or more mols based on 1 mol of the ester compound given by formula (1), or is usually 1 or more mols based on 1 mol of the ester compound given by formula (2) in case that the second step is carried out without isolating the product after the first step.

In the reaction, it is preferable that an alcohol (e.g. methanol, ethanol, propanol) is further added in an amount of 0.3 part by weight or more based on 1 part by weight of the ester compound given by formula (1), or 0.3 part by weight or more based on 1 part by weight of the ester compound given by formula (2) in case that the second step is carried out without isolating the product after the first step, in the view of the reaction rate.

The reaction temperature is usually in the range of 0 to 40° C., and the reaction period is usually in the range of 0.5 to 24 hours.

The reaction is, for example, carried out as follows.

(1) A method of dissolving the compound given by formula (1) in a solvent, adding an aqueous solution of an alkali metal hydroxide thereto and stirring the mixture (2) A method of optionally adding a solvent to the reaction product in the first step, and further adding an aqueous solution of an alkali metal hydroxide thereto and stirring the mixture The concentration of the aqueous solution of an alkali metal hydroxide used for the method (1) or (2) is usually 5 to 49% by weight.

The proceeding status of the reaction can be confirmed by means for analyzing the reaction mixture such as high performance liquid chromatography, gas chromatography and the like.

After the reaction, the compound given by formula (3) can be isolated by work-up procedures, for example, obtaining an organic layer by water-organic solvent phase separation of the reaction mixture, optionally washing the organic layer with aqueous acid, and concentrating the organic layer.

According to the production method of 3,5-dichloro-4-(3-hydroxypropoxy)-1-substituted-benzenes described in U.S. Pat. No. 5,827,137, the crystals consisting of by-products, i.e. sodium benzoate and inorganic salt, are occasionally precipitated during the reaction or work-up procedures to make the operation more difficult, and it needs a large amount of water for the purpose of removing by-products by the phase-separation during the work-up procedures. To the contrary, the production method 2 of the present invention does not give the crystals to make the operation more difficult or does not need a large amount of water in the phase-separation during the work-up procedures. It is beneficial concerning dealing waste water.

The 3-phenoxypropanol compound given by formula (3) produced by the production method 2 of the present invention can be lead to the dihalopropene compounds having insecticidal/acaricidal activity by the methods described in U.S. Pat. No. 5,827,137 and U.S. Pat. No. 5,922,880.

The compounds given by formula (2) are the compounds described in U.S. Pat. No. 5,827,137 and U.S. Pat. No. 5,922,880 or can be prepared according to their descriptions.

EXAMPLES

The present invention is explained in detail below and the present invention is not limited to the following examples. In the examples, "%" means "% by weight" until especially explained.

Example 1

A mixture of 1.09 parts by weight of 3,5-dichloro-4-(3-chloropropoxy)-1-(3,3-dichloro-2-propenyloxy)benzene given by formula (4)

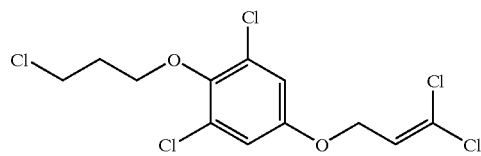

(purity, 91.7%) with 0.16 part by weight of toluene, 0.044 part by weight of tetra-n-butylammonium bromide and 0.34 part by weight of sodium acetate were charged in a reaction vessel, and stirred under nitrogen atmosphere at 103–105° C. for 14 hours. Then, the reaction mixture was allowed to be cooled and 1.0 part by weight of 2% aqueous sodium hydroxide solution and 2.7 parts by weight of toluene were added thereto. The organic layer was separated, washed with 2.0 parts by weight of 5% sulfuric acid and 2.0 parts by weight of water subsequently, and then concentrated to make the total residue 2.29 parts by weight. A portion of the residue was subjected to silica gel column chromatography to give 7.78 g of 3,5-dichloro-4-(3-acetyloxypropoxy)-1-(3,3-dichloro-2-propenyloxy)benzene given by formula (5)

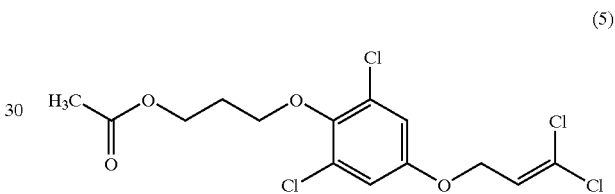

Further, the analysis of the above-mentioned residue by liquid chromatography showed that the content of 3,5-dichloro-4-(3-acetyloxypropoxy)-1-(3,3-dichloro-2-propenyloxy)benzene was 44.97% (yield, 96.7%).

The melting point of 3,5-dichloro-4-(3-acetyloxypropoxy)-1-(3,3-dichloro-2-propenyloxy)benzene was 33° C.

Example 2

A mixture of 1.09 parts by weight of 3,5-dichloro-4-(3-chloropropoxy)-1-(3,3-dichloro-2-propenyloxy)benzene (purity, 91.7%) with 0.16 part by weight of toluene, 0.044 part by weight of tetra-n-butylammonium bromide and 0.34 part by weight of sodium acetate were charged in a reaction vessel, and stirred under nitrogen atmosphere at 103–105° C. for 13 hours. Then, the reaction mixture was allowed to be cooled to 25–30° C. and 0.5 part by weight of methanol and 0.3 part by weight of toluene were added thereto. Further, 0.46 part by weight of 29% aqueous sodium hydroxide solution were added to the reaction mixture and stirred at the same temperature for 2 hours. To the reaction mixture, 1.0 part by weight of 2% aqueous sodium hydroxide solution and 2.7 parts by weight of toluene were added. The organic layer was separated, washed with 5% sulfuric acid and 2.0 parts by weight of water subsequently, and then concentrated to make the total residue 2.18 parts by weight. The residue was analyzed by liquid chromatography to show that the content of 3,5-dichloro-4-(3-hydroxypropoxy)-1-(3,3-dichloro-2-propenyloxy)benzene given by formula (6)

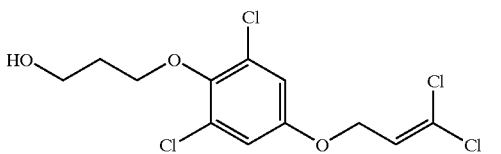

was 42.12%. The yield from 3,5-dichloro-4-(3-chloropropoxy)-1-(3,3-dichloro-2-propenyloxy)benzene was 96.5%.

Example 3

In a reaction vessel, 1.06 parts by weight of 3,5-dichloro-4-(3-chloropropoxy)-1-benzyloxybenzene (purity, 94.7%) of formula (7)

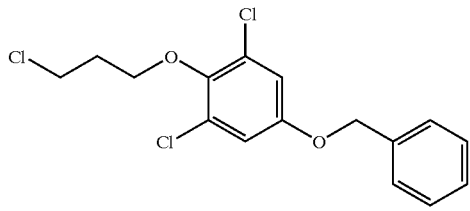

0.19 part by weight of toluene, 0.047 part by weight of tetra-n-butylammonium bromide and 0.36 part by weight of sodium acetate were charged and stirred under nitrogen atmosphere at 103–105° C. for 11 hours. Then, the reaction mixture was allowed to be cooled to 25–30° C. and 0.5 part by weight of methanol and 0.3 part by weight of toluene were added thereto. Further, 0.47 part by weight of 29% aqueous sodium hydroxide solution was added dropwise and stirred at the same temperature for 2 hours. To the reaction mixture, 1.0 part by weight of 2% aqueous sodium hydroxide solution and 2.7 parts by weight of toluene were added. The organic layer was separated, washed with 2.0 parts by weight of 5% sulfuric acid and 2.0 parts by weight of water subsequently, and then concentrated to make the total residue 0.98 part by weight. The residue was analyzed by liquid chromatography to show that the content of 3,5-dichloro-4-(3-hydroxypropoxy)-1-benzyloxybenzene given by formula (8)

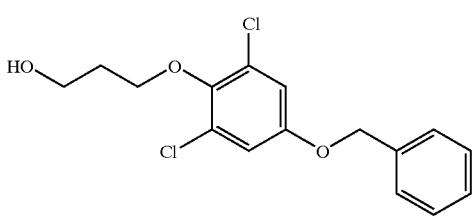

was 94.66%. The yield from 3,5-dichloro-4-(3-chloropropoxy)-1-benzyloxybenzene was 98.4%.

The analysis condition in the examples above is as follows.
Check of the Reaction Proceeding It was analyzed by high performance liquid chromatography in the following condition.
Used apparatus: L-6000 or L-7000 manufactured by Hitachi Corp.
Column: L-column ODS (4.6φ×150 mm, manufactured by Chemicals Inspection & Testing Institute)
Column temperature: 40° C.
Detector: UV (Detected wave length: 290 nm)
Mobile phase: 0.1% phosphoric acid/water (hereinafter referred to as Solution A) and 0.1% phosphoric acid/acetonitrile (hereinafter referred to as Solution B) were prepared and used in the ratio given below.
① From 0 min. to 25 min. of retention time, Solution A/Solution B was gradually changed from 1/1 to 0/1.
② From 25 min. to 35 min. of retention time, Solution A/Solution B was kept at 0/1.
③ From 35 min. to 35.1 min. of retention time, Solution A/Solution B was gradually changed from 0/1 to 1/1.
④ After 35.1 min. of retention time, Solution A/Solution B was kept at 1/1.
Flow rate of mobile phase: 1.0 ml/min.
Analysis of the Content of the Product
(1) Analysis of the content of 3,5-dichloro-4-(3-acetyloxypropoxy)-1-(3,3-dichloro-2-propenyloxy)benzene It was analyzed by high performance liquid chromatography in the following condition.
Internal standard: isoamyl benzoate
Used apparatus: L-6000 or L-7000 manufactured by Hitachi Corp.
Column: L-column ODS (4.6 φ×150 mm, manufactured by manufactured by Chemicals Inspection & Testing Institute)
Column temperature: 40° C.
Detector: UV (Detected wave length: 290 nm)
Mobile phase: 0.1% phosphoric acid/water (hereinafter referred to as Solution A) and 0.1% phosphoric acid/acetonitrile (hereinafter referred to as Solution B) were prepared and used in the ratio given below.
① From 0 min. to 30 min. of retention time, Solution A/Solution B was kept at 35/65.
② From 30 min. to 30.1 min. of retention time, Solution A/Solution B was changed from 35/65 to 0/1.
③ From 30.1 min. to 45 min. of retention time, Solution A/Solution B was kept at 0/1.
④ From 45 min. to 45.1 min. of retention time, Solution A/Solution B was changed from 0/1 to 35/65.
⑤ After 45.1 min. of retention time, Solution A/Solution B was kept at 35/65.
Flow rate of mobile phase: 1.0 ml/min.
(2) Analysis of the content of 3,5-dichloro-4-(3-hydroxypropoxy)-1-(3,3-dichloro-2-propenyloxy)benzene and 3,5-dichloro-4-(3-hydroxypropoxy)-1-benzyloxybenzene It was analyzed by high performance liquid chromatography in the following condition.
Internal standard: isoamyl benzoate
Used apparatus: L-6000 or L-7000 manufactured by Hitachi Corp.
Column: L-column ODS (4.6 φ×150 mm, manufactured by manufactured by Chemicals Inspection & Testing Institute)
Column temperature: 40° C.
Detector: UV (Detected wave length 290 nm)
Mobile phase: 0.1% phosphoric acid/water (hereinafter referred to as Solution A) and 0.1% phosphoric acid/acetonitrile (hereinafter referred to as Solution B) were prepared and used in the ratio given below.
① From 0 min. to 30 min. of retention time, Solution A/Solution B was kept at 45/55.
② From 30 min. to 30.1 min. of retention time, Solution A/Solution B was changed from 45/55 to 0/1.
③ From 30.1 min. to 45 min. of retention time, Solution A/Solution B was kept at 0/1.
④ From 45 min. to 45.1 min. of retention time, Solution A/Solution B was changed from 0/1 to 45/55.

⑤ After 45.1 min. of retention time, Solution A/Solution B was kept at 45/55.

Flow rate of mobile phase: 1.0 ml/min.

According to the production method of the present invention, 3,5-dichloro-4-(3-hydroxypropoxy)-1-substituted-benzenes which are useful as intermediates for insecticide/acaricide can be beneficially produced in industry.

We claim:

1. A method for the production of an ester compound given by formula (1):

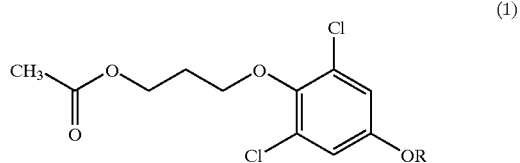
(1)

wherein R represents a 3,3-dihalo-2-propenyl group or a benzyl group optionally substituted by at least one halogen atom, which comprises making a compound given by formula (2):

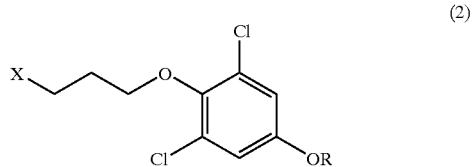
(2)

wherein X represents a chlorine atom or bromine atom and R means as described below
react with an alkali metal salt of acetic acid in the presence of an aromatic hydrocarbon.

2. The method according to claim 1, wherein R represents a 3,3-dihalo-2-propenyl group.

3. The method according to claim 1, wherein R represents a 3,3-dichloro-2-propenyl group.

4. The method according to claim 1, wherein R represents a benzyl group optionally substituted by at least one halogen atom.

5. The method according to claim 1, wherein R represents a benzyl group or 4-chlorobenzyl group.

6. The method according to claim 1, wherein R makes the reaction in the presence of a phase transfer catalyst as well as aromatic hydrocarbon.

7. A method for the production of a 3-phenoxypropanol compound given by the formula (3):

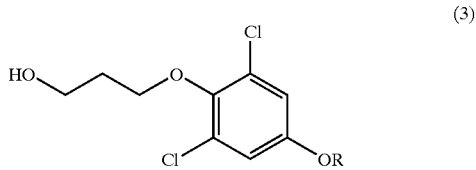
(3)

wherein R means as described below, which comprises making a compound given by formula (2):

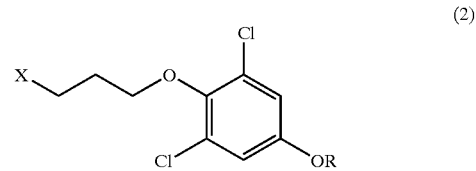
(2)

wherein X represents a chlorine atom or bromine atom and R represents a 3,3-dihalo-2-propenyl group or a benzyl group optionally substituted by at least one halogen atom, react with an alkali metal salt of acetic acid in the presence of an aromatic hydrocarbon, and then making the product react with an alkali metal hydroxide and water.

8. An ester compound given by formula (1):

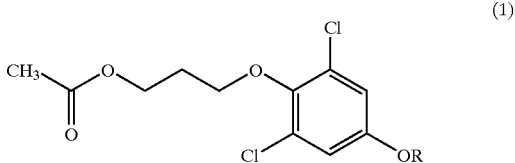
(1)

wherein R represents a 3,3-dihalo-2-propenyl group or a benzyl group optionally substituted by at least one halogen atom.

* * * * *